United States Patent
Edelman et al.

(10) Patent No.: US 8,838,204 B2
(45) Date of Patent: Sep. 16, 2014

(54) SYSTEM AND METHOD FOR PHASE CONTRAST IMAGING WITH IMPROVED EFFICIENCY

(71) Applicants: Robert R Edelman, Highland Park, IL (US); Christopher Glielmi, Hoboken, NJ (US); Ioannis Koktzoglou, Rolling Meadows, IL (US); Erik J Offerman, Chicago, IL (US)

(72) Inventors: Robert R Edelman, Highland Park, IL (US); Christopher Glielmi, Hoboken, NJ (US); Ioannis Koktzoglou, Rolling Meadows, IL (US); Erik J Offerman, Chicago, IL (US)

(73) Assignees: Siemens Medical Solutions USA, Inc., Malvern, PA (US); The United States of America as represented by the National Institutes of Health (NIH), Washington, DC (US); U.S. Dept of Health and Human Services (DHHS), Washington, DC (US)

(*) Notice: Subject to any disclaimer, the term of this patent is extended or adjusted under 35 U.S.C. 154(b) by 17 days.

(21) Appl. No.: 13/718,141

(22) Filed: Dec. 18, 2012

(65) Prior Publication Data
US 2013/0184561 A1    Jul. 18, 2013

Related U.S. Application Data

(60) Provisional application No. 61/586,310, filed on Jan. 13, 2012.

(51) Int. Cl.
*A61B 5/026*     (2006.01)
*G01R 33/563*    (2006.01)
*A61B 5/0402*    (2006.01)
*A61B 5/00*      (2006.01)
*G01R 33/567*    (2006.01)

(52) U.S. Cl.
CPC ............. *A61B 5/0263* (2013.01); *A61B 5/0044* (2013.01); *G01R 33/5635* (2013.01); *A61B 5/7285* (2013.01); *G01R 33/5673* (2013.01); *A61B 5/0402* (2013.01)
USPC ........... 600/413; 600/407; 600/410; 600/419; 382/131; 324/309

(58) Field of Classification Search
CPC .. A61B 5/0044; A61B 5/0263; A61B 5/0402; A61B 5/7285; G01R 33/5635
USPC .................. 600/407, 410, 413, 419; 382/131; 324/309
See application file for complete search history.

(56) References Cited

U.S. PATENT DOCUMENTS

| 8,163,003 B2 | 4/2012 | Boyden et al. |
| 2007/0112264 A1* | 5/2007 | Wu et al. ....................... 600/410 |

(Continued)

OTHER PUBLICATIONS

Nielsen JF, Nayak KS, Referenceless phase velocity mapping using balanced SSFP. Magn. Reson. Med, May 2009; 61(5): 1096-102.

*Primary Examiner* — Baisakhi Roy
(74) *Attorney, Agent, or Firm* — Peter R. Withstandley (57) ABSTRACT

A system and method is provided for magnetic resonance angiography (MRA) that includes performing a pulse sequence using the MRI system, the pulse sequence including a phase-based flow encoding to collect a time-series of image data from the portion of the vasculature of the subject and identifying at least a portion of the time series of image data corresponding to a period of reduced flow through the portion of the vasculature. The portion of the time series of image data is subtracted from the time series of image data to create a time series of images of the portion of the vasculature having background tissue surrounding the portion of the vasculature substantially suppressed.

9 Claims, 4 Drawing Sheets

(56) References Cited

U.S. PATENT DOCUMENTS

2008/0021502 A1 1/2008 Imielinska et al.
2008/0262341 A1 10/2008 Boyden et al.
2010/0312098 A1* 12/2010 Miyazaki .................. 600/413
2012/0212222 A1 8/2012 Subramanian et al.
2012/0281901 A1* 11/2012 Yoshizawa et al. .......... 382/131
2013/0147481 A1* 6/2013 Miyawaki et al. ........... 324/309

* cited by examiner

SYSTEM AND METHOD FOR PHASE CONTRAST IMAGING WITH IMPROVED EFFICIENCY

CROSS-REFERENCE TO RELATED APPLICATIONS

This application is a non-provisional of, and claims priority to, U.S. provisional patent application Ser. No. 61/586,310 by Robert R. Edelman et al. filed on 13 Jan. 2012.

This invention was made with government support under HL096916 awarded by National Institutes of Health. The government has certain rights in the invention.

FIELD OF THE INVENTION

The invention relates to a system and method for performing magnetic resonance angiography (MRA) and, more particularly, to a system and method for MRA that utilizes phase-based flow encoding but does not require acquisition of two separate data sets for the purposes of image subtraction, thereby improving imaging efficiency and reducing artifacts.

BACKGROUND OF THE INVENTION

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Magnetic resonance angiography (MRA) uses the NMR phenomenon to produce images of the human vasculature. There are three main categories of techniques for achieving the desired contrast for the purpose of MR angiography. The first general category is typically referred to as contrast enhanced (CE) MRA. The second general category is time-of-flight (TOF) MRA. The third general category is phase contrast (PC) MRA.

To perform CE MRA, a contrast agent, such as gadolinium, is injected into the patient prior to the magnetic resonance (MR) angiogram to enhance the diagnostic capability of the MR angiogram. While CE MRA is a highly effective means for noninvasively evaluating suspected vascular disease, the technique suffers from several additional drawbacks. First, the contrast agent that must be administered to enhance the blood vessel carries a significant financial cost. Second, contrast agents such as gadolinium have recently been shown to be causative of an often catastrophic disorder called nephrogenic systemic fibrosis (NSF). Third, CE MRA does not provide hemodynamic information, so that it is not always feasible to determine if a stenosis is hemodynamically significant. Fourth, the signal-to-noise ratio (SNR) and, therefore, spatial resolution is limited by the need to acquire data quickly during the first pass of contrast agent through a target vessel. For these reasons, there have been substantial efforts to move away from CE MRA imaging protocols in favor of non contrast-enhanced (NCE) MRA protocols.

Fortunately, TOF and PC MRA imaging techniques do not require the use of a contrast agent. The 3D TOF techniques were introduced in the 1980's and they have changed little over the last decade. The 3D TOF MRA techniques commonly used for cranial examinations and have not been replaced despite recent advances in time-resolved contrast-enhanced 3D MRA. An alternative technique known as pulsed arterial spin labeling (PASL) was first applied to image intracranial circulation years ago; however, image quality never approached that of 3D TOF and the method has had little clinical utility. Moreover, electrocardiographic (ECG) gating was required. The use of TOF MRA is generally limited to imaging of intracranial circulation, however, because of sensitivity to patient motion and flow artifacts.

Finally, phase contrast (PC) MRA is largely reserved for the measurement of flow velocities and imaging of the vasculature. Phase contrast sequences are the basis of MRA techniques utilizing the change in the phase shifts of the flowing protons in the region of interest to create an image. Spins that are moving along the direction of a magnetic field gradient receive a phase shift proportional to their velocity. Specifically, in a PC MRA pulse sequence, two data sets with different amounts of flow sensitivity are acquired. This is usually accomplished by applying gradient pairs, which sequentially dephase and then rephase spins during the sequence. The first data set is acquired using a "flow-compensated" pulse sequence or a pulse sequence without sensitivity to flow. The second data set is acquired using a pulse sequence designed to be sensitive to flow. The amount of flow sensitivity is controlled by the strength of the bipolar gradient pulse pair use in the pulse sequence because stationary tissue undergoes no effective phase change after the application of the two gradients, whereas the different spatial localization of flowing blood is subjected to the variation of the bipolar gradient. Accordingly, moving spins experience a phase shift. The raw data from the two data sets are subtracted to yield images that illustrate the phase change, which is proportional to spatial velocity.

Thus, to perform PC MRA pulse sequences, a substantial scan time is generally required and the operator must set a velocity-encoding sensitivity, which varies unpredictably depending on a variety of clinical factors. The necessity of acquiring two data sets negatively affects the temporal resolution by a factor of two. Moreover, the two acquisitions use different gradient waveforms (e.g. a flow-encoded data set uses a bipolar gradient whereas a flow-rephased data set uses three gradient lobes). Consequently, gradient-induced eddy currents are not identical for the two acquisitions, which results in spatially and time-varying background phase shifts despite the use of image subtraction. Such background phase shifts cause errors in the velocity measurement and necessitate the use of complex phase correction algorithms.

Accordingly, several attempts have been made to utilize a "referenceless" phase contrast MRI technique. For instance, Nielsen J F, Nayak K S, Referenceless phase velocity mapping using balanced SSFP. Magn. Reson. Med, 2009 May; 61(5): 1096-102, uses a balanced SSFP pulse sequence with the requirement that the echo time (TE) be equal to one-half of the repetition time (TR). The use of a bSSFP sequence is not desirable because of an intrinsic sensitivity to artifacts from off-resonance effects and increased artifacts from gradient-induced eddy currents compared with a spoiled gradient-echo acquisition. Moreover, the method requires the manual placement of regions of interest near blood vessels and additional processing with a phase correction algorithm. Even with all these steps, the background phase correction is not uniform.

Therefore, it would be desirable to have a system and method for decreasing the acquisition time of phase-based, flow-encoding, imaging techniques that does not correspondingly increase artifacts in the resulting images.

SUMMARY OF THE INVENTION

The present invention overcomes the aforementioned drawbacks by providing a system and method for In accordance with one aspect of the invention, a method is provided for acquiring a magnetic resonance angiography (MRA) image of a portion of a vasculature of a subject using a magnetic resonance imaging system. The method includes performing a pulse sequence using the MRI system, the pulse sequence including a phase-based flow encoding to collect a time-series of image data from the portion of the vasculature of the subject. The method also includes identifying at least a portion of the time series of image data corresponding to a period of reduced flow through the portion of the vasculature. The method further includes subtracting the portion of the time series of image data from the time series of image data to create a time series of images of the portion of the vasculature having background tissue surrounding the portion of the vasculature substantially suppressed.

In accordance with another aspect of the invention, a magnetic resonance imaging (MRI) system is disclosed that includes a magnet system configured to generate a polarizing magnetic field about at least a portion of a subject arranged in the MRI system, a plurality of gradient coils configured to apply a gradient field to the polarizing magnetic field, a radio frequency (RF) system configured to apply an excitation field to the subject and acquire MR image data therefrom, and computer system. The computer system is programmed to perform a pulse sequence using the MRI system, the pulse sequence including a phase-based flow encoding to collect a time-series of image data from the portion of the vasculature of the subject. The computer system is also programmed to identify at least a portion of the time series of image data corresponding to a period of reduced flow through the portion of the vasculature. The computer system is further programmed to subtract the portion of the time series of image data from the time series of image data to create a time series of images of the portion of the vasculature having background tissue surrounding the portion of the vasculature substantially suppressed.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
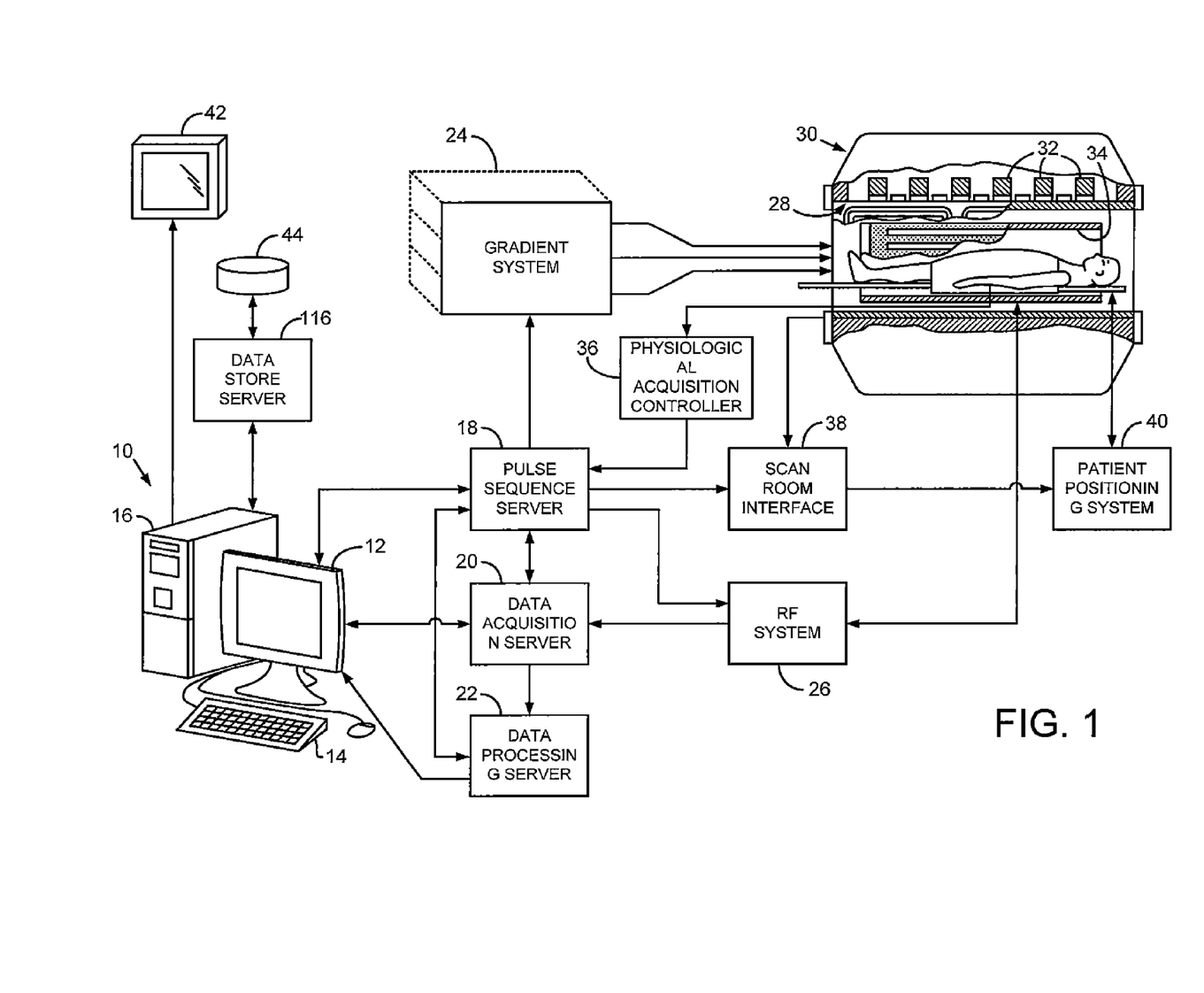
FIG. 1 is a block diagram of an MRI system for use with the present invention.

Referring particularly to FIG. 1, the invention is employed in an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system.

The workstation 10 is coupled to, for example, four servers, including a pulse sequence server 18, a data acquisition server 20, a data processing server 22, and a data store server 23. The servers 18, 20, 22, and 23 may be physically embodied as individual server systems or may be representations of one or more physical server systems. In one configuration, the data store server 23 is performed by the workstation processor 16 and associated disc drive interface circuitry and the remaining three servers 18, 20, 22 are performed by one or more separate servers.

The workstation 10 and each of the servers 18, 20, 22, and 23 are connected to a communications network. This network conveys data that is downloaded to the servers 18, 20, 22, and 23 from the workstation 10 and conveys data that is communicated between the servers 18, 20, 22, and 23 and between the workstation 10 and the servers 18, 20, 22, and 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$, and $G_z$ used for position encoding NMR signals. The gradient coil assembly 28 forms part of a magnet assembly 30, which includes a polarizing magnet 32 and a whole-body RF coil 34.

The RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered, and digitized under direction of commands produced by the pulse sequence server 18. The RF system 26 includes an RF transmitter for producing a wide variety of RF pulses used in MR pulse sequences. The RF system 26 is responsive to the scan prescription and direction from the pulse sequence server 18 to produce RF pulses of the desired frequency, phase, and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector that detects and digitizes the in-phase (I) and quadrature (Q) components of the received NMR signal. The magnitude of the received NMR signal may thus be determined at any sampled point by the square root of the sum of the squares of the I and Q components.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates in response to description components downloaded from the workstation 10 to receive the real-time NMR data. In some scans, the data acquisition server 20 does little more than pass the acquired NMR data to the data processor server 22. However, in scans that require information derived from acquired NMR data to control the further performance of the scan, the data acquisition server 20 may be programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. Furthermore, the data acquisition server 20 may be employed to process NMR signals used to detect or determine subsequent acquisition timings. In all these examples the data acquisition server 20 acquires NMR data and processes it in, for example, real-time to produce information that is used to control the scan.

The data processing server 22 receives NMR data from the data acquisition server 20 and processes it in accordance with description components downloaded from the workstation 10. Such processing may include, for example, Fourier transformation of raw k-space NMR data to produce two or three-dimensional images, the application of filters to a reconstructed image, the performance of a backprojection image reconstruction of acquired NMR data, the calculation of functional MR images, the calculation of motion or flow images, and the like.

Images reconstructed by the data processing server 22 are conveyed back to the workstation 10. Real-time images may be output to operator display 12 or a display 42 that is located near the magnet assembly 30 for use by attending physicians. Batch mode images or selected real-time images may be stored in a host database on disc storage 44. When such images have been reconstructed and transferred to storage 44, the data processing server 22 notifies the data store server 23 on the workstation 10. The workstation 10 may be used by an operator to archive the images or send the images via a network to other facilities.

Figure 2:
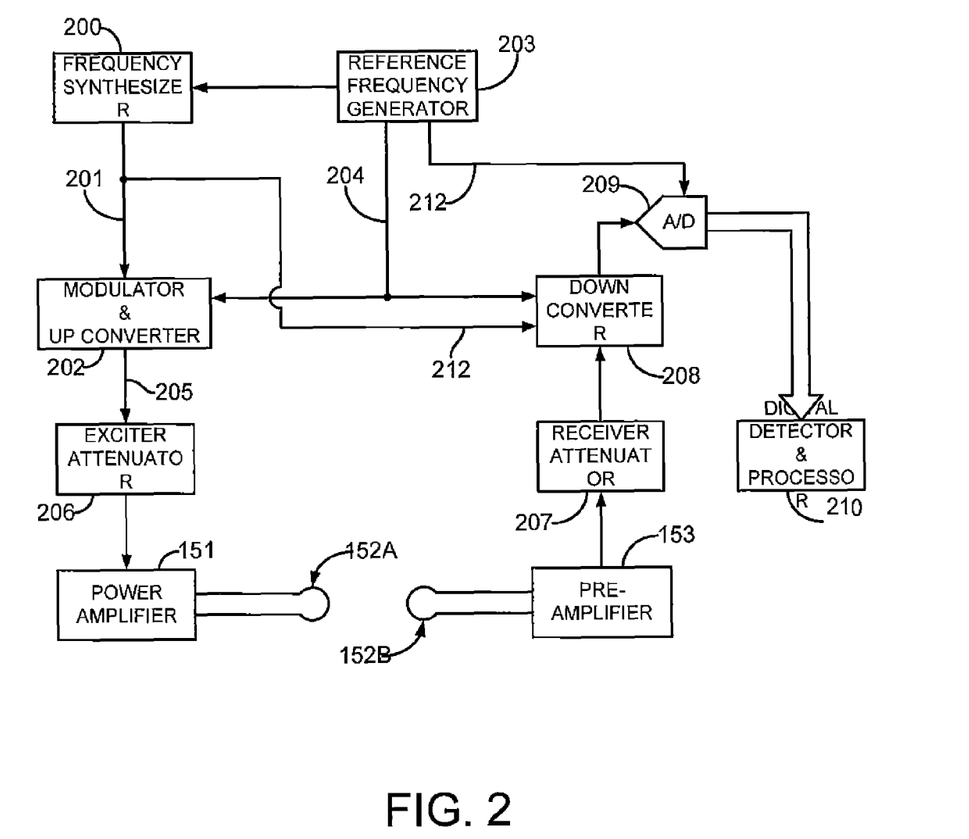
FIG. 2 is a schematic representation of a transceiver system for use with the MRI system of FIG. 1.

As shown in FIG. 1, the RF system 26 may be connected to the whole body RF coil 34, or as shown in FIG. 2, a transmitter section of the RF system 26 may connect to one RF coil 151A and its receiver section may connect to a separate RF receive coil 151B. Often, the transmitter section is connected to the whole body RF coil 34 and each receiver section is connected to a separate local coil 151B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 151A.

Referring still to FIG. 2, the signal produced by the subject is received by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high-frequency signal is down converted in a two step process by a down converter 208 that first mixes the NMR signal with the carrier signal on line 201 and then mixes the resulting difference signal with a reference signal on line 204. The down converted NMR signal is applied to the input of an analog-to-digital (A/D) converter 209 that samples and digitizes the analog signal and applies it to a digital detector and signal processor 210 to produce the I values and Q values corresponding to the received signal. As described above, the resulting stream of digitized I and Q values of the received signal are output to the data acquisition server 20 of FIG. 1. The reference signal, as well as the sampling signal applied to the A/D converter 209, is produced by a reference frequency generator 203.

Figure 3:
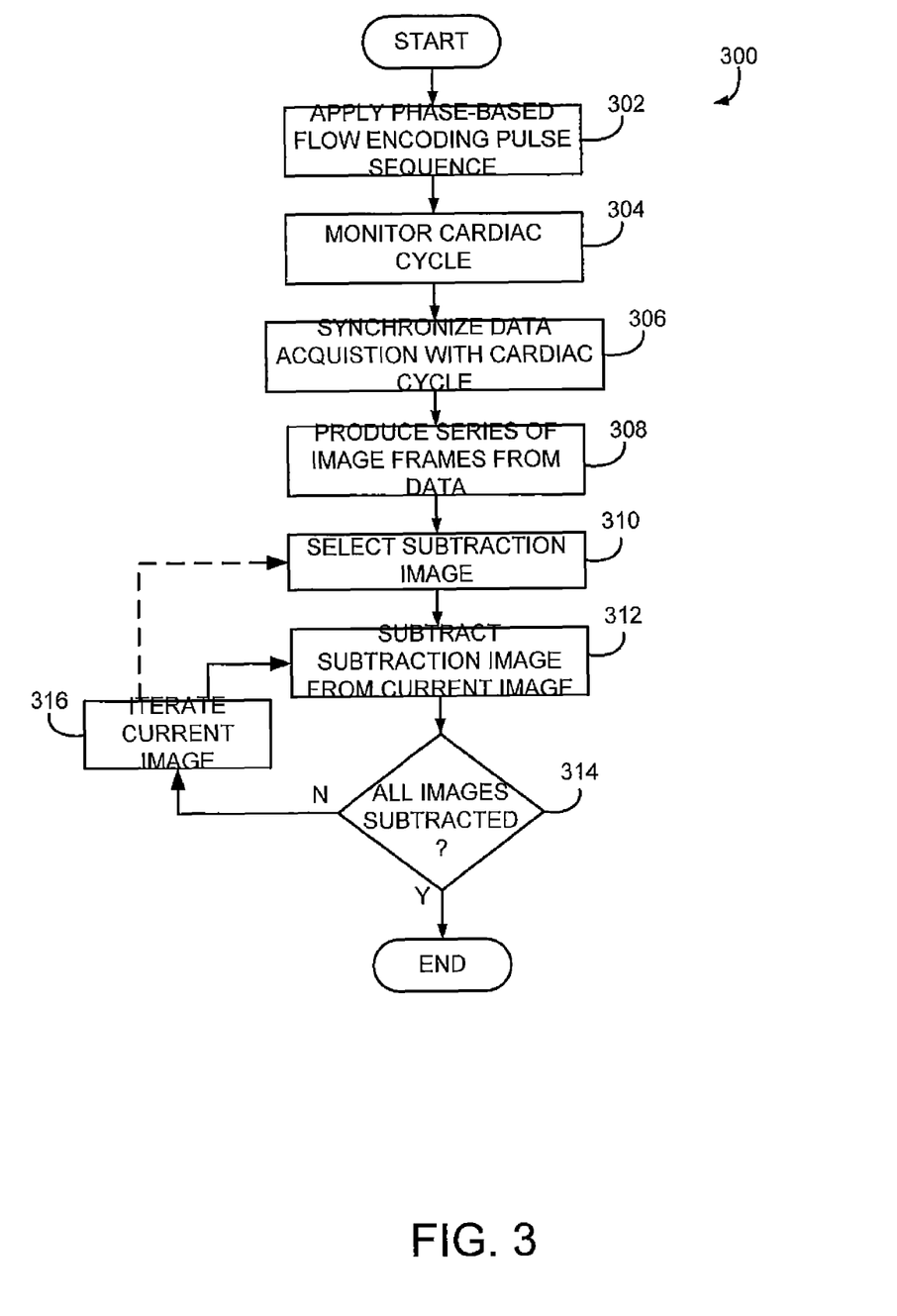
FIG. 3 is a flow chart of the steps performed in accordance with one exemplary implementation of the present invention.
Figure 4:
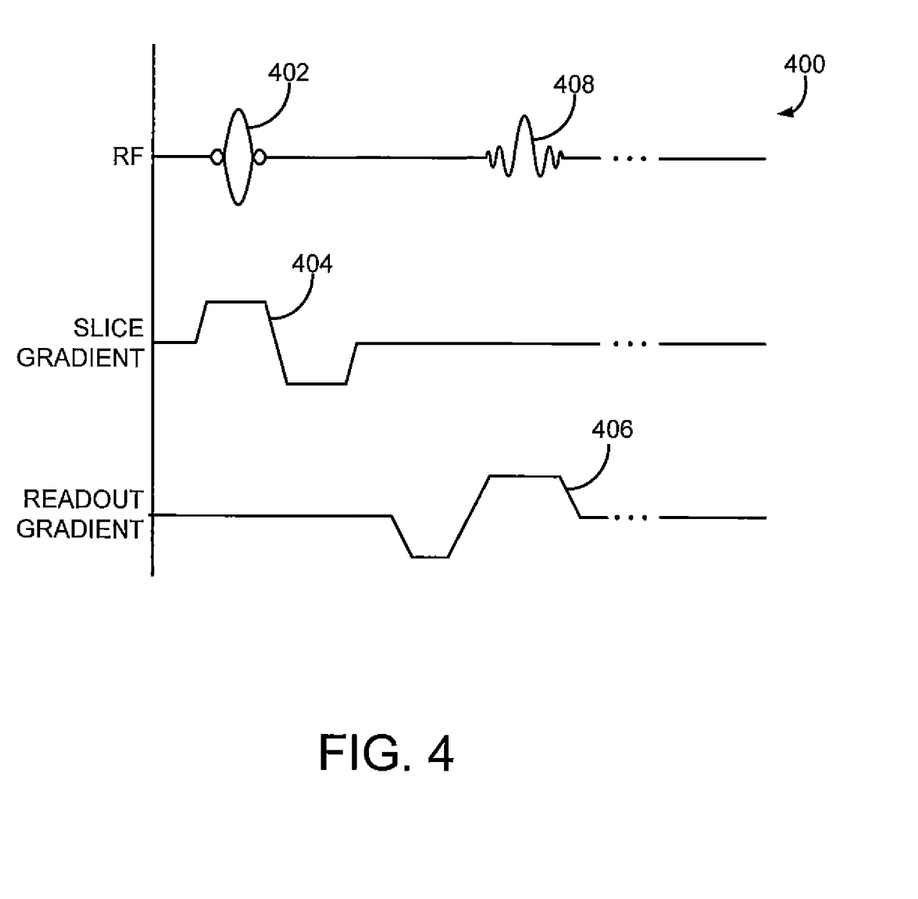
FIG. 4 is a diagram illustrating a pulse sequence performed by the MRI system of FIG. 1 in accordance with the present invention.

As mentioned, the present invention provides a system and method for phase-based, flow-encoded, imaging techniques that alleviates the need for performing two separate and distinct data acquisitions for the purposes of image subtraction. Specifically, referring to FIG. 3, a method 300 in accordance with the present invention begins by applying a pulse sequence designed for phase-based flow encoding at process block 302. For example, a gradient-echo pulse sequence 400, such as illustrated in FIG. 4, may be used. The gradient-echo pulse sequence 400 includes an imaging RF pulse 402 timed with a motion compensated gradient 404 along the slice-selection gradient. Thus, one or more bipolar gradients 402 may be applied along one or more directions, such as the slice-selection direction for measurement of through-plane flow in order to encode flow. A readout gradient 406 is applied to acquire the desired NMR signal 408.

Referring again to FIG. 3, during the performance of the above-described pulse sequence or similar sequences, the cardiac cycle is monitored, as indicated at process block 304. As will be described, this monitoring may occur according to one or more methods. For example, non-imaging-based monitoring may be performed to monitor the cardiac cycle, such as electrophysiological monitoring. Also, image-based monitoring may be performed, such as using navigators or other imaging-based tracking methodologies. Regardless of the particular monitoring methods or systems utilized, the cardiac monitoring performed at process block 304 is used to then synchronize data acquisition to the cardiac cycle at process block 306. That is, the data acquisition illustrated by the acquisition of the NMR signal 408 in FIG. 4, is synchronized to the cardiac cycle. This synchronization may be performed in a manner similar to a conventional phase contrast MRI acquisition, such that a series of images (or "frames") are produced at process block 308 representing sequential temporal phases of blood flow over the heart cycle.

At process block 310 a subtraction image is selected. For example, one frame or several frames averaged together to form a common image may be selected to represent a temporal phase of the cardiac cycle for subtraction from the time series of motion encoded image frames. For example, an image frame may be selected or common image frame of multiple averaged images may be selected such that has very low or no flow within a vessel of interest.

At process block 312, the subtraction image frame (or average of several frames) is subtracted from a current image frame. At decision block 314, a check is made to determine if the current image frame was the last image frame. If not, the current image or image frame is iterated at process block 316 and the new current image or image frame is subtracted at process block 312. This process is repeated until each of the subsequent frames is subtracted such that the time series of images is produced in which background phase shifts are suppressed.

It is noted that when the current image or image frame is iterated at process block 316, it may be desirable to select another subtraction or create a new average of several image frames and, thus, the process may continue to process block 310. Such an optional process may be desirable, for example, to allow a clinician the option to acquire flow rephased reference data in a minority of frames (typically one or just a few) which allows for correction of the flow velocities in setting where the minimum flow velocity is non-zero. By comparison, with standard phase contrast flow measurement, an equal number of flow encoded and rephased frames would be alternately acquired at process block 302.

Compared with conventional phase contrast MRI, the present invention has several advantages. For example, the present invention improves temporal resolution by a factor of two. Also, by eliminating the need for a three-lobed gradient for the flow-rephased acquisition, the minimum echo time is reduced. Use of a shorter echo time is advantageous for suppressing phase shifts due to magnetic susceptibility effects. Furthermore, because identical gradient waveforms are played out for each frame, gradient-induced eddy currents are substantially equivalent in all frames and do not contribute to background phase shifts. This reduces the need for additional background phase corrections and improves the accuracy of the method compared with previously described approaches.

It is noted that the present invention presupposes a condition such that at least one frame be acquired during a phase of the cardiac cycle when flow is minimal or absent. When imaging, for example, the heart or the peripheral arteries, this may be a clinical constraint. That is, the clinic an will need to plan for the collection and identification of the low or now flow image, such as using monitoring systems or acquiring additional images or frames or, at a minimum, selecting a desirable frame. However, if imaging under conditions where the minimum arterial flow velocity never approaches zero, then absolute flow velocity quantification will not be obtained. Nonetheless, under such conditions, one can always determine the pulse wave amplitude over the cardiac cycle, which is often of equal or greater clinical importance in comparison with absolute velocity measurement, and use such to designate or create a desired subtraction image. Alternatively, one can use the process described above to ensure that absolute flow velocities are determined, even when a condition of absent flow does not exist.

The present invention has been described in terms of one or more preferred embodiments, and it should be appreciated that many equivalents, alternatives, variations, and modifications, aside from those expressly stated, are possible and within the scope of the invention.

The invention claimed is:

1. A method of acquiring a magnetic resonance angiography (MRA) image of a portion of a vasculature of a subject using a magnetic resonance imaging (MRI) system, the method comprising:
    performing a pulse sequence using the MRI system, the pulse sequence including a phase-based flow encoding to collect a time-series of image data from the portion of the vasculature of the subject;
    monitoring, during the performing of the pulse sequence, a cardiac cycle of the subject and synchronizing the collection of the time-series of image data from the portion of the vasculature of the subject to the cardiac cycle of the subject;
    identifying at least a portion of the time series of image data within the cardiac cycle and corresponding to a period of reduced flow through the portion of the vasculature; and
    subtracting the portion of the time series of image data within the cardiac cycle from the time series of image data to create a time series of images of the portion of the vasculature having background tissue surrounding the portion of the vasculature substantially suppressed.

2. The method of claim 1 wherein identifying at least a portion of the time series of image data includes selecting at least one image frame to create a subtraction image.

3. The method of claim 2 wherein subtracting includes subtracting the subtraction image from each image frame reconstructed from the time series of image data.

4. The method of claim 2 wherein identifying at least a portion of the time series of image data includes selecting multiple image frames and averaging the multiple image frames to create a subtraction image.

5. The method of claim 4 wherein subtracting includes subtracting the subtraction image from each image frame reconstructed from the time series of image data.

6. The method of claim 1 wherein identifying includes selecting at least one image frame from a time series of images reconstructed from the time series of image data corresponding to reduced flow from through the portion of the vasculature.

7. The method of claim 1 wherein subtracting includes iteratively processing each image frame reconstructed from the time series of image data with respect to the identified at least a portion of the time series of image data.

8. The method of claim 1 wherein a minority of image frames is acquired using a flow-rephased gradient waveform.

9. A magnetic resonance imaging (MRI) system comprising:
    a magnet system configured to generate a polarizing magnetic field about at least a portion of a subject arranged in the MRI system;
    a plurality of gradient coils configured to apply a gradient field to the polarizing magnetic field;
    a radio frequency (RF) system configured to apply an excitation field to the subject and acquire MR image data therefrom;

a computer system programmed to:
perform a pulse sequence using the MRI system, the pulse sequence including a phase-based flow encoding to collect a time-series of image data from the portion of the vasculature of the subject;
monitor, during the performing of the pulse sequence, a cardiac cycle of the subject and synchronize the collection of the time-series of image data from the portion of the vasculature of the subject to the cardiac cycle of the subject;
identify at least a portion of the time series of image data within the cardiac cycle and corresponding to a period of reduced flow through the portion of the vasculature; and
subtract the portion of the time series of image data within the cardiac cycle from the time series of image data to create a time series of images of the portion of the vasculature having background tissue surrounding the portion of the vasculature substantially suppressed.

* * * * *